United States Patent [19]
Araujo et al.

[11] Patent Number: 6,001,755
[45] Date of Patent: Dec. 14, 1999

[54] METHOD OF MAKING A UV ABSORBING LIQUID

[75] Inventors: Roger J. Araujo, Horseheads, N.Y.; Alain R. E. Carre, Le Chatelet-en-Brie; Serge A. M. Renault, Montigny sur Loing, both of France

[73] Assignee: Corning Incorporated, Corning, N.Y.

[21] Appl. No.: 09/117,888

[22] PCT Filed: Feb. 11, 1997

[86] PCT No.: PCT/US97/01680

§ 371 Date: Aug. 7, 1998

§ 102(e) Date: Aug. 7, 1998

[87] PCT Pub. No.: WO97/30946

PCT Pub. Date: Aug. 28, 1997

Related U.S. Application Data

[60] Provisional application No. 60/011,966, Feb. 21, 1996, and provisional application No. 60/020,654, Jun. 27, 1996.

[51] Int. Cl.$^6$ ...................................................... C03C 8/16
[52] U.S. Cl. .............................. 501/77; 510/77; 510/905; 424/59; 252/588; 252/589; 523/122; 523/135; 106/15.05; 106/18.3; 524/494
[58] Field of Search ................................ 501/20, 77, 905; 424/59; 252/588, 589; 523/122, 135; 106/15.05, 18.3; 524/494

[56] References Cited

U.S. PATENT DOCUMENTS

| | | |
|---|---|---|
| 4,166,745 | 9/1979 | Araujo et al. . |
| 4,222,781 | 9/1980 | Morse et al. . |
| 4,859,637 | 8/1989 | Roberts . |
| 5,145,805 | 9/1992 | Tarumi et al. . |
| 5,322,819 | 6/1994 | Araujo et al. . |
| 5,366,660 | 11/1994 | Tapley . |
| 5,541,142 | 7/1996 | Araujo . |

FOREIGN PATENT DOCUMENTS

| | | |
|---|---|---|
| 356092968 | 7/1981 | Japan . |
| 401297179 | 11/1989 | Japan . |

*Primary Examiner*—Karl Group
*Attorney, Agent, or Firm*—Angela N. Nwaneri

[57] ABSTRACT

The invention relates to a thin layer of UV absorbing material, and a method of making such material by grinding UV absorbing glass into fine powder which can be suspended in a liquid matrix, for example, in index matching oil, thereby producing a transparent liquid which can be used to coat any material to impart UV absorption to such material.

15 Claims, No Drawings

METHOD OF MAKING A UV ABSORBING LIQUID

This application claims the benefit of U.S. Provisional Application No. 60/011,996, filed Feb. 21, 1996, entitled "Method of Making a UV Absorbing Liquid" and Provisional Application No. 60/020,654 filed Jun. 27, 1996.

BACKGROUND OF THE INVENTION

Recently, a great deal of attention has been directed to the harmful effects of ultraviolet (UV) radiation on humans. Much of the attention has concerned the effect of such radiation on the eye. Accordingly, the value of strong UV absorption by eye glasses has been recognized.

It is well known that UV radiation can also cause degradation and discoloration in such items as paints, fabrics and plastics. Therefore, strong UV absorption by architectural glazing materials is beneficial. The sun is not the only light source that emits UV. Various types of artificial lighting, such as halogen lamps, may also emit UV radiation. Accordingly, there is an interest in minimizing UV radiation emitted by artificial sources as well. This may be achieved by utilizing UV absorbing glass in the fabrication of lamp envelopes, reflectors and lenses.

It is common knowledge that photochromic glasses are activated by absorption of UV radiation. The most evident utility of such glasses has been in control of visible light transmission. Inherently, however, they also strongly influence the intensity of UV transmission. This behavior is readily understood in terms of the Grotthus-Draper Law which states that: Only light that is absorbed can produce chemical change.

Photochromic glasses containing silver halide crystals absorb strongly at wavelengths shorter than 320 nm, but only absorb weakly in the interval between 320 and 400 nm. Even though radiation in the wavelength range of 320–400 nm is much less eliminate transmission of this radiation as well. Therefore, several suggestions have been advanced for accomplishing this. For example, it has been proposed to dope the above glasses with ions which provide additional absorption of UV radiation.

Photochromic glasses containing halides of copper and/or cadmium are also known, but not commercially available. Such glasses were originally disclosed in U.S. Pat. No. 3,325,299 (Araujo I). The transmission cutoff in these glasses occurs at approximately 400 nm, and is much sharper than that in silver halide glasses. Consequently, protection against UV radiation is complete in these glasses without additional doping. The precipitation of the copper halide phase in these glasses is like that of the silver halide phase in the silver halide photochromic glasses. It may require heating of a glass containing in solution the copper and halogen ions of interest. As taught in the patent, the glass is maintained for a short time at a temperature somewhat above the annealing point.

U.S. Pat. No. 4,166,745 (Araujo II) discloses copper-cadmium photochromic glasses that have a refractive index of 1.52–1.54, and that may be strengthened by an exchange of sodium ions for lithium ions.

U.S. Pat. No. 4,222,781 (Morse et al.) discloses photochromic glasses based on copper halide wherein good optical clarity and photochromic properties are provided by controlling the alkali metal oxide, the $Al_2O_3$ and the $B_2O_3$ concentrations in the base glass, and/or by adding $MoO_3$ or $WO_3$ to the composition.

European Publication Number 0 456 351 A2 [U.S. Pat. No, 5,145,805] (Tarumi et al) discloses two glass families containing up to 15% copper halide. The non-phosphate family comprises, in percent by weight, 20–85% $SiO_2$, 2–75% $B_2O_3$, up to 15% $Al_2O_3$, up to 30% alkali metal oxides, up to 10% divalent metal oxides and up to 10% of at least one of $ZrO_2$, $La_2O_3$, $Y_2O_3$, $Ta_2O_3$ and $Gd_2O_3$.

There are numerous applications for glasses having the sharp UV cutoff inherent in the copper or copper-cadmium halide glasses. Frequently, however, such applications require avoiding any change in visible absorption such as occurs in photochromic glasses exposed to UV radiation, e.g., sunlight. Many UV materials exhibit yellow color which is unacceptable for certain applications. U.S. Pat. No. 5,322,819 (Araujo III) disclosed a non-photochromic, copper halide containing UV absorbing glass which exhibits a sharp cutoff in ransmission in the wavelength interval between visible and UV radiation. Specifically, the Araujo III reference ('819) disclosed a non-photochromic $R_2O$—$B_2O_3$—$SiO_2$ glass which contains a precipitated cuprous or cuprous-cadmium halide crystal phase and has a sharp spectral cutoff at about 400 nm, the glass composition consisting essentially of, in cation percent, 35–73% $SiO_2$, 15–45% $B_2O_3$, 0–12% $Al_2O_3$, the $Al_2O_3$ being less than 10% when the $SiO_2$ is over 55%, 0–12% $Li_2O$, 0–20% $Na_2O$, 0–12% $K_2O$, the $Li_2O+Na^2O+K_2O$ being 4.75–20%, 0–5% $CaO+BaO+SrO$, 0.125–1.0% $Cu_2O$, 0–1% CdO, 0–5% $ZrO_2$, 0–0.75% $SnO_2$, 0–1% $As_2O_3$, and/or $Sb_2O_3$, the glass containing 0–1.25% Cl, 0–1.0% Br, 0.25–2.0Cl+Br and 0–2% F by weight.

UV absorbing glasses are generally available in bulk form, making then impractical for certain applications such as UV absorbing paints and varnishes as well as UV absorbing skin creams for example. Accordingly, it is a principal object of the present invention to provide UV absorbing glass in a form which can be readily utilized in such applications.

SUMMARY OF THE INVENTION

The object of the present invention is achieved by providing UV absorbing glass in a form suitable for protecting from UV radiation, articles having complicated shapes. Examples of suitable forms of the inventive UV absorbing glass material include, (1) a liquid such as a lotion or cream for protecting the skin, (2) paints and varnishes for applying over articles having complicated shapes and sizes, and (3) a solution with which clothing materials can be impregnated to form UV absorbing clothing.

Briefly, the invention relates to a UV absorbing solution comprising, (a) fine particles of a strong UV absorbing glass consisting essentially of, in cation percent, 15–30% $SiO_2$, 50–60% $B_2O_3$, 2–5% $Al_2O_3$, 0–6% $Li_2O$, 0–3.0% $Na_2O$, 14–20% $K_2O$, 0.5–1.0% CuO, 0.4–0.7% $SnO_2$, 0.5–1.5% Cl, and 0.7–1.5% Br; and (b) a matrix into which the fine glass particles are suspended or dissolved to form the UV absorbing solution.

In another aspect, the invention relates to a method of making UV absorbing liquid or gel by:
  a) providing a UV absorbing glass;
  b) grinding the glass into fine powder having average particle size in the range of 1–5 microns; and
  c) suspending the fine powder in a matrix to form a liquid or gel.

In still another aspect, the invention relates to a method of producing essentially haze-free (i.e., transparent), strong UV absorbing glass by:
  a) providing a strong UV absorbing glass having a known refractive index, and containing copper and halides;

b) melting the glass;

c) quenching the glass by rolling said glass into a thin roll or ribbon; and d) heat treating said ribbon to form an essentially haze-free, UV absorbing glass.

The heating process leads to the growth of copper halide crystals in the glass.

In a further aspect, the invention relates to a method of making a transparent UV absorbing liquid by:

a) providing a strong UV absorbing glass composition consisting essentially of, in cation percent, 15–30% $SiO_2$, 50–60% $B_2O_3$, 2–5% $Al_2O_3$, 0–6% $Li_2O$, 0–0.7% $Na_2O$, 14–20% $K_2O$, 0.5–1.0% CuO, 0.4–0.7% $SnO_2$, 0.5–1.5% Cl, and 0.7–1.5% Br;

b) melting the glass;

c) forming the melt into a thin sheet of glass to quench the glass;

d) heat treating the glass to grow tiny crystals of CuCl in the glass;

e) grinding the heat-treated sheet of glass into fine powder having average particle size in the range of 1–5 microns;

f) suspending the fine powder in a transparent liquid to form a transparent UV absorbing liquid.

In still a further aspect, the invention relates to a method of protecting an article from UV radiation by applying a coating of the inventive Uv absorbing liquid on the surface of the article to be protected.

DETAILED DESCRIPTION OF THE INVENTION

UV absorption in transparent colorless glasses that strongly absorb UV radiation, such as disclosed in U.S. Pat. No. 5,322,819, is due to the suspension of minute crystallites of cuprous halides. Previous attempts to make photochromic plastics by suspending finely ground photochromic glass failed because when the photochromic glass was ground sufficiently fine to make transparent suspensions in organic matrices, no photochromism was observed. Further, the finely ground photochromic glass exhibited a noticeable grey color. Although the reason for this loss of photo-chromism and color change was never shown, it is widely believed that radiation associated with fast crack propagation during the grinding process photolyzed the silver halide suspended in the glass thereby producing the grey color and destroying photochromism.

With this background, it was not clear that UV absorbing materials can be made by suspending finely ground powders of UV absorbing glass in a matrix without a similar loss of the UV absorbing properties. Thus, the first part of the present invention was to determine whether grinding would destroy the cuprous halide particles in UV absorbing glass in the same way silver halide particles were destroyed in photochromic glasses. This is the subject of Example 1 below. As described in the example, grinding does not destroy cuprous halide crystalites. Without intending to be bound by theory, we believe that unlike the situation in photochromic glasses, in these glasses, radiation does not photolyze the crystallites. The sharp UV absorption observed in these glasses correspond to exciton formation. The exciton energy is immediately dissipated in the excitation of lattice modes and the crystal relaxes to its ground state. Thus, even if grinding does generate energetic radiation, photolysis of the cuprous halide is unlikely to pose a problem.

Another question investigated was whether a higher density of cuprous halide particles could be precipitated in glass than had been previously produced. This was important because, unless this could be done, the strength of the UV absorption in thin films would be too weak for many of the intended applications. Accordingly, we have discovered that a family of glasses which contain very high levels of boric oxide and relatively low levels of silica exhibit much stronger UV absorption than currently available UV absorbing glasses. Examples of this family of glasses are described in Table 1 below.

TABLE 1

(In cation %, except for the halides which are given in weight %)

| Oxide | Comparative Glass 1 | Glass 2 | Glass 3 | Glass 4 | Glass 5 |
|---|---|---|---|---|---|
| $SiO_2$ | 57.5 | 22.0 | 22.0 | 22.0 | 22.5 |
| $B_2O_3$ | 26.0 | 55.4 | 55.4 | 55.4 | 55.4 |
| $Al_2O_3$ | 2.0 | 3.0 | 3.0 | 3.0 | 3.0 |
| $ZrO_2$ | 3.0 | — | — | — | — |
| $Li_2O$ | 2.5 | — | 2.0 | 5.0 | 2.0 |
| $Na_2O$ | 7.5 | 0.5 | 0.5 | 0.5 | 0.5 |
| $K_2O$ | 1.5 | 19.1 | 17.1 | 14.1 | 17.1 |
| CuO | 0.35 | 0.65 | 0.65 | 0.65 | 0.85 |
| $SnO_2$ | 0.2 | 0.43 | 0.43 | 0.43 | 0.6 |
| Cl | 0.75 | 1.0 | 1.0 | 1.0 | 1.0 |
| Br | 1.0 | 1.0 | 1.0 | 1.0 | 1.0 |

It is known that the precipitation of either silver halide or cuprous halide is stimulated by a change in bonding of boron during the heat treatment of the glass. As a result, the amount of halide precipitated tends to increase as the amount of boric oxide in the glass increases. For this reason, the inventive glass composition is preferably low in silica and high in boric oxide.

Another class of inventive glasses are those having high levels of copper and halides. While strong UV absorption was observed in this class of inventive glass, we have found that as the precipitated cuprous halide increases, the haze level of the glass also increases. This family of strong UV absorbing glasses generally consist of, expressed in cation percent, 15–30% $SiO_2$, 50–60% $B_2O_3$, 2–5% $Al_2O_3$, 0–6% $Li_2O$, 0–3.0% $Na_2O$, 14–20% $K_2O$, 0.5–1.0% CuO, 0.4–0.7% $SnO_2$, 0.5–1.5% Cl, and 0.7–1.5% Br. It should be noted that the higher the amount of $Na_2O$, the lower the UV absorption of the glass. In one particularly useful embodiment, the preferred range of $Na_2$ is in the range of 0.2–0.7%.

We have discovered that if the glasses are quenched from the melt (for example, by rolling them into thin ribbons), and subsequently heating the rolled glass for very long times at low temperatures, strong UV absorption can be obtained with relatively low levels of haze. This is illustrated in Examples 3 and 4 below. By way of example, one method of rolling the glass is by pouring the melt into a steel plate and rolling the melt with a steel roller. The act of rolling quenches (or quickly cools) the glass and keeps it transparent. Haze is maintained at a low level by avoiding large crystal growths in the glass. The low temperature treatment of the rolled glass allows tiny copper halide crystals (e.g., CuCl) crystals to grow such that strong UV absorption is achieved without haze.

As stated, the higher the levels of copper and halides, the higher the level of haze in the glass. Thus, it is expected that even stronger UV absorption as those measured in the aforementioned glass composition can be achieved by substantially increasing the amounts of copper and halides in the glass. However, because it is not possible to measure UV absorption level in opaque glasses, we are unable to define the upper limit of copper and halides, or even to determine if such a limit exists for UV absorption purposes. As a result, in those applications where transparency is not essential or even useful, for example, where the UV absorbing glass is to be added to paints, lotions and the like, significantly higher amounts of both copper and halides can be added. For example, it is expected that for such applications, copper in the amount of up to 5% or greater, and halides up to 3% or greater can be used.

For applications where it is not practical to apply a roll or ribbon of the UV absorbing glass over the article to be protected from UV radiation, the UV absorbing glass ribbon can be ground into a fine powder which can subsequently be suspended in a matrix to form a UV absorbing liquid which can then be applied to the surface of the article to be protected.

For applications requiring transparency, the refractive index of the matrix is preferably the same or substantially the same as that of the UV absorbing glass. A particularly useful matrix for such applications is index matching oil. Examples of applications where use of the liquid form may be useful include, UV absorbing paints and varnishes, UV absorbing body lotions or creams, as a spray for such objects as automobiles and boats, and other similar applications. The matrix can be in any suitable form for a given application. For example, the matrix can be aqueous or non-aqueous, polymeric or non-polymeric, and can be in the form of a gel or a liquid, for example.

The heat treated rolled glass or ribbon of glass can optionally, be ground into a fine powder having an average particle size, preferably in the range of 1–5 microns. If it is desired to form a UV absorbing liquid for example, the glass powder can be suspended in a matrix such as a liquid, to form a UV absorbing liquid. As contemplated by this invention, the powder may be added for example, to body lotion to make such lotion UV absorbing to thereby protect the skin from UV radiation. In addition, the powder may be added to a paint or varnish to make the paint and varnish UV absorbing. Another contemplated use of the inventive UV absorbing liquid is for example, application to an article of clothing to thereby make such clothing UV absorbing. The above examples of possible uses of the inventive UV absorbing liquid are by way of illustration only, they are not exhaustive. Other similar applications will be obvious to persons skilled in the art.

In one preferred embodiment, a transparent UV absorbing liquid was formed by melting a glass composition consisting essentially of, in cation percent, 15–30% $SiO_2$, 50–60% $B_2O_3$, 2–5% $Al_2O_3$, 0–6% $Li_2O$, 0–3.0% $Na_2O$, 14–20% $K_2O$, 0.5–1.0% CuO, 0.4–0.7% $SnO_2$, 0.5–1.5% Cl and 0.7–1.5% Br; forming the melt into a thin sheet of glass to quickly quench the glass; heat treating the quenched sheet of glass at a temperature of 525° C. for about 96 hours; grinding the heat treated sheet to an average particle size of 3 microns; and suspending the ground glass in a matrix of index matching oil. A film or coating of the resulting transparent UV absorbing liquid can then be applied over the surface of any support or article to be protected from UV absorption. Preferably such coating is in the range of 0.1 to 1 mm in thickness.

We have found that by mixing fine particles of UV absorbing glass in a polymeric matrix a transparent or translucent coating suitable for protecting wood surfaces from photodegradation. At coating thicknesses as low as 100 microns, the glass/polymer composite exhibits very low UV transmission. For this embodiment, the volume fraction and size distribution of the glass will depend on the level of UV protection desired. Preferably, the glass volume fraction is such that at a coating thickness of 50–300 μm, the coating absorbs at least 75% of the UV radiation. It may be necessary to use a coupling agent to stabilize the glass dispersion and improve the mechanical resistance of the glass/polymer coating. While the glass/polymer composite may exhibit some haze, the final coating preferably exhibits sufficient translucence to avoid altering the natural appearance and natural appearance of the wood. As stated earlier, to achieve good transparency, the refractive index of the polymer phase is matched against that of the UV absorbing glass. The polymer/glass coating can be applied to the wood surface by any suitable methods such as painting, spraying and dipping.

Various aspects of the invention will now be described by reference to the following examples, using the glass compositions given in Table 1.

EXAMPLES

Example 1

The purpose of this experiment was to determine if the process of grinding degraded the strength of the UV absorbance of glass.

A comparative UV absorbing glass (Glass 1), having the following composition: 57.5% $SiO_2$, 26% $B_2O_3$, 2.0% $Al_2O_3$, 3.0% $ZrO_2$, 2.5% $Li_2O$, 7.5% $Na_2O$, 1.5% $K_2O$, 0.35% CuO, 0.2% $SnO_2$, 0.75% Cl, and 1.0% Br, was ground to an average particle size of 3 microns and suspended in index matching oil. The suspension comprised 15 percent by weight ground glass. The density of the oil was 0.88 gms/cc. The density of the glass was assumed to be 2.4 gm/cc. Thus the volume fraction was 0.55. The transmittance spectrum of this material was then measured.

The absorption coefficient of the bulk glass at 380 nm was 112.6 $cm^{-1}$ whereas the absorption coefficient for the ground glass was determined to be 121.9 $cm^{-1}$. The agreement is within empfltal error. Thus, unlike photochromic glasses, UV absorbing glasses can be ground with no degradation of the strength of the UV absorbance.

Example 2

The purpose of this experiment was to determine whether a coating or thin film of the glass suspension of Example 1 would be effective in reducing the UV transmittance of an optical glass having such coating or film applied to its surface.

A coating of the glass suspension of Example 1, one millimeter thick was applied to the surface of a microscope slide. The UV transmittance of the glass was reduced by about a factor of two.

Example 3

The purpose of this experiment was to show that the quenching of the glass prior to heat treatment is effective in maintaining a low haze level.

A quenched thin nbbon of the inventive glass (Glass 5) whose composition is given in Table 1 above, was heat treated at 525° C. for 72 hours. It was ground down to a thickness of about 0.25 mm, and a standard haze test registered 1.16%.

A four millimeter thick piece of the same glass given the same heat treatment and then ground to a thickness of about 0.25 mm. A haze of 5.52% was measured.

Example 4

The purpose of this experiment was to demonstrate the efficacy of the inventive glass and heat treatment.

A quenched thin ribbon of Glass 5 was heat treated at 525° C. for 96 hours. The UV absorption coefficient was found to be 357 cm$^{-1}$. This represents an improvement by a factor of 3.2 over that of the comparative glass of Example 1.

As shown by the above examples, the inventive glasses exhibit very strong UV absorption, in many cases, absorption coefficients exceeding 250 cm$^{-1}$ at 385 nm were observed. The observed absorption coefficient is significantly higher than observed in glasses such as Glass 1 which are intended for use in liquid crystal display, and other applications. As shown in Example 1, the measured absorption coefficient for such glass was in the region of 100 cm$^{-1}$.

Example 5

The purpose of this experiment was to determine the effect of grinding on the UV absorbing properties of the inventive glass.

The glass of Examples 3 and 4 (Glass 5), was ground to an average particle size of 3 microns and suspended in transparent index matching oil so that the suspension comprised about 15 weight percent, ground glass. As in Example 1, the density of the oil was 0.88 gm/cc. The density of Glass 5 is estimated at about 2.4 g/cc, so that the volume fraction of the suspension was about 0.55%. The transmittance spectrum of the matrix was then measured.

The observed absorption coefficient was 178 cm$^{-1}$. In this liquid state, the improvement over the UV absorption of the comparative glass of Example 1, dropped to a factor of 1.5. It is not known why the UV absorption coefficient of glass differs in the suspension (Example 5), from the value measured in bulk (Examples 3 and 4).

As contemplated by the invention, this liquid combination of UV absorbing glass and a matrix such as the transparent index matching oil, can be applied to the surface of any article to protect the article from UV radiation. For transparent applications, the matrix should have the same index as the glass to ensure transparency.

Example 6

In this example, a sheet of UV cut-off glass was ground to an average particle size in the range of 1–2 $\mu$m. The glass particles were then added to a polymeric matrix comprising a vinylic-versatic-acrylic terpolymer aqueous dispersion. The volume ratio of the glass in the matrix was in the range of 30–55%. Wood samples were then coated with the resulting glass/polymer composite, and dried to obtain a final dried coating having a thickness in the range of 100–200 $\mu$m. The coating was sufficiently translucent that after coating, the wood retained its natural appearance.

In other variants of this example, silane coupling agents were added to the -glass/polymer miuture in amounts in the range of 0.1–2 wt %, preferably in the range of 0.2–wt %, to stabilize the glass dispersion and improve the mechanical properties of the coating. Examples of suitable silane coupling agents for the glass/polymer mixture of Example 6, include γ-aminopropyltrialkoxysilane, and methacryloxypropyltrialkoxysilane. The inventive glass/polymer composite can also be formulated using any polymeric solution, emulsion or dispersion used for wood protection or decoration.

In addition to the embodiments discussed above, it will be clear to persons skilled in the art that numerous modifications and changes can be made to the above invention without departing from its intended spirit and scope.

We claim:

1. UV absorbing liquid dispersion comprising UV absorbing glass consisting assembly of, in cation percent, 15–30% SiO$_2$, 50–60% B$_2$O$_3$, 2–5% Al$_2$O$_3$, 0–6% Li$_2$O, 0–3.0% Na$^2$O, 14–20% K$_2$O, 0.5–5.0% CuO, 0.4–0.7% SnO$_2$, 0.5–3.0% Cl, and 0.7–3.0% Br.

2. UV absorbing liquid dispersion of claim 1, wherein the UV absorbing glass consisting essentially of 0.5–1.0% CuO, 0.2–0.7% Na$_2$O, 0.5–1.5% Cl, and 0.7–1.5% Br.

3. UV absorbing liquid dispersion of claim 1, wherein said glass has an average particle size in the range of 1–5 microns.

4. A method of forming a transparent UV absorbing liquid comprising the steps of:
   a) providing a UV absorbing gas having a known refractive index and comprising copper and a halide;
   b) melting the glass;
   c) forming the melt into a thin sheet of glass to quench the glass;
   d) heat treating the glass to grow tiny crystals of copper halide in the glass;
   e) grinding the heat-treated sheet of glass into fine powder having average particle size in the range of 1–5 microns; and
   f) suspending the fine powder in a matrix to form a UV absorbing liquid.

5. Tho method of claim 4, wherein the glass consists essentially of, in caton percents, 15–30% SiO$_2$, 50–60% B$_2$O$_3$, 2–5% Al$_2$O$_3$, 0–6% Li$_2$O, 0.2–0.7% Na$_2$O, 14–20% K$_2$O, 0.5–1.0% CuO, 0.4–0.7% SnO$_2$, 0.5–1.5% Cl, and 0.7–1.5% Br.

6. The method of claim 4, wherein the matrix is a liquid having a refractive index substantially equal to the refractive index of the glass.

7. The method of claim 6, wherein the matrix is an index matching oil.

8. A method of protecting an article from UV radiation by:
   a) providing a UV absorbing glass consisting essentially of, in cation percent, 15–30% SiO$_2$, 50–60% B$_2$O$_3$, 2–5% Al$_2$O$_3$, 0–6% Li$_2$O, 0.2–0.7% Na$_2$O, 14–20% K$_2$O, 0.5–1.0% CuO, 0.4–0.7% SnO$_2$, 0.5–1.5% Cl, and 0.7–1.5% Br.;
   b) grinding the glass into fine powder;
   c) suspending the fine porwder in a matrix to form a UV absorbing liquid; and
   d) applying a coating of the liquid onto a surface of the article.

9. The method of claim 8, prior to the grinding step, further comprising the steps of:
   a) melting the glass;
   b) forming the melt into a thin sheet of glass to quench the glass; and
   c) heat treating the thin sheet of glass which is then ground into fine powder.

10. The method of claim 8, wherein the coating is about 0.1 to 1 mm in thickness.

11. A method of forming a UV absorbing coating suitable for protecting wood from photodegradation, the method conprising the steps of:
   a) providing a UV absorbing glass having a known refractive index and comprising copper and a halide;
   b) meaning the glass;

c) forming the melt into a thin sheet of glass to quench the glass;

d) heat treating the glass to grow tiny crystals of copper halide in the glass;

e) grinding the heat-treated sheet of glass into fine powder having average particle size in the range of 1–5 microns; and f) suspending the fine powder in a polymeric matrix to form a UV absorbing coating.

12. The method of claim 11, wherein the matrix further comprises a coupling agent.

13. The method of claim 12, wherein the coupling agent is a silane compound.

14. The method of claim 13, wherein the silane compound is present in an amount in the range of 0.1 to 1.5 wt. %, and is selected from the group consisting of γ-aminopropyltrialkoxysilane and methacryloxypropyltrialkoxysilane.

15. The method of claim 11, wherein the glass is present in the polymeric matrix in a volume ratio in the range of 30 to 55%.

* * * * *

UNITED STATES PATENT AND TRADEMARK OFFICE
CERTIFICATE OF CORRECTION

PATENT NO. : 6,001,755
DATED : December 14, 1999
INVENTOR(S) : Roger J. Araujo, Alain R. E. Carre and Serge A. M. Renault It is certified that error appears in the above-identified patent and that said Letters Patent is hereby corrected as shown below:

| Col. | Line | |
|---|---|---|
| 8 | 7 | Change "Na$^2$O" to --Na$_2$O-- |
| 8 | 17 | Change "gas" to --glass-- |
| 8 | 31 | Change "caton" to --cation-- |

Signed and Sealed this

Twenty-sixth Day of September, 2000

Attest:

Q. TODD DICKINSON

Attesting Officer      *Director of Patents and Trademarks*